(12) United States Patent
Chen et al.

(10) Patent No.: US 9,105,563 B2
(45) Date of Patent: Aug. 11, 2015

(54) METHOD AND SYSTEM OF IMPROVED UNIFORMITY TESTING

(71) Applicant: Intermolecular, Inc., San Jose, CA (US)

(72) Inventors: Charlene Chen, San Jose, CA (US); Tony P. Chiang, Campbell, CA (US); Chi-I Lang, Cupertino, CA (US); Yun Wang, San Jose, CA (US)

(73) Assignee: Intermolecular, Inc., San Jose, CA (US)

( * ) Notice: Subject to any disclaimer, the term of this patent is extended or adjusted under 35 U.S.C. 154(b) by 399 days.

(21) Appl. No.: 13/713,421

(22) Filed: Dec. 13, 2012

(65) Prior Publication Data

US 2013/0122614 A1    May 16, 2013

Related U.S. Application Data

(62) Division of application No. 12/957,354, filed on Nov. 30, 2010, now Pat. No. 8,370,096.

(51) Int. Cl.
| | |
|---|---|
| *G01N 21/59* | (2006.01) |
| *H01L 21/66* | (2006.01) |
| *H01L 29/16* | (2006.01) |
| *H01L 21/02* | (2006.01) |

(52) U.S. Cl.
CPC .............. *H01L 22/20* (2013.01); *G01N 21/59* (2013.01); *H01L 22/12* (2013.01); *H01L 29/1606* (2013.01); *H01L 21/0262* (2013.01); *H01L 21/02491* (2013.01); *H01L 21/02527* (2013.01)

(58) Field of Classification Search
USPC .......................................................... 702/81
See application file for complete search history.

(56) References Cited

PUBLICATIONS

Helgi Skuli Skulason, Optical Properties of Few and Many Layer Graphene Flakes, Department of Electrical & Computer Engineering McGill University Montreal, Canada, Sep. 2009, 84 pages.*

* cited by examiner

*Primary Examiner* — Tung S Lau

(57) ABSTRACT

A method and system includes a first substrate and a second substrate, each substrate comprising a predetermined baseline transmittance value at a predetermine wavelength of light, processing regions on the first substrate by combinatorially varying at least one of materials, process conditions, unit processes, and process sequences associated with the graphene production, performing a first characterization test on the processed regions on the first substrate to generate first results, processing regions on a second substrate in a combinatorial manner by varying at least one of materials, process conditions, unit processes, and process sequences associated with the graphene production based on the first results of the first characterization test, performing a second characterization test on the processed regions on the second substrate to generate second results, and determining whether at least one of the first substrate and the second substrate meet a predetermined quality threshold based on the second results.

19 Claims, 8 Drawing Sheets

METHOD AND SYSTEM OF IMPROVED UNIFORMITY TESTING

CROSS-REFERENCE TO RELATED APPLICATIONS

This application is a Divisional Application of U.S. patent application Ser. No. 12/957,354, filed on Nov. 30, 2010, which is herein incorporated by reference for all purposes.

BACKGROUND

1. Technical Field

The embodiments herein generally relate to semiconductor processing and characterization, and more specifically, to an improved system and method for uniformity testing of semiconductor substrates.

2. Description of the Related Art

The ability to process uniformly across a monolithic substrate and/or across a series of monolithic substrates is advantageous for manufacturing efficiency and cost effectiveness, as well as repeatability and control. However, uniform processing across an entire substrate can be disadvantageous when optimizing, qualifying or investigating new materials, new processes, and/or new process sequence integration schemes, since the entire substrate is nominally made the same using the same materials, processes, and process sequence integration schemes. Each processed substrate generally represents, in essence, only one possible variation per substrate. Thus, the full wafer uniform processing under conventional processing techniques results in fewer data points per substrate, longer times to accumulate a wide variety of data, and higher costs associated with obtaining such data.

For example, characterizing graphene (e.g., characterizing graphene uniformity) is an important, yet time consuming using conventional systems. For example, one conventional system for characterizing graphene includes atomic force microscopy (AFM). Conventional uses of AFM to characterize graphene, however, typically suffer from a low throughput, are time-consuming characterization methods, and could damage the sample during testing. Conventional systems also use ellipsometry, and optical microscopy to characterize graphene. For ellipsometry, to determine the graphene thickness, optical properties (refractive index and absorption constant) for each sample typically must be known first, which is a time-consuming process when testing multiple samples because the optical properties may change from sample to sample. In addition, the optical response for very thin films (e.g., <20 Å) is often buried in noise. For optical microscopy, the contrast of graphene films generally has to be optimized for characterization by adjusting the underlying dielectric material, thickness, and the light wavelength used, which is also a time-consuming process. Due to the time-consuming and destructive nature of conventional systems, a wafer can generally only be used to evaluate a single process condition using conventional technology. Generally, the unit processes and test workflows (e.g., combinatorial workflows) used in current industry are complicated, time-consuming, and not cost efficient when using conventional technologies. For example, to know the result of each condition, one wafer with many follow-up steps is required, which under current technology is very complicated as well as cost inefficient. In particular, semiconductor companies conduct research and development (R&D) on full wafer processing through the use of split lots, as the deposition systems are designed to support this processing scheme. This approach has resulted in high R&D costs and the inability to conduct extensive experimentation in a timely and cost effective manner.

BRIEF DESCRIPTION OF THE DRAWINGS

The embodiments herein will be better understood from the following detailed description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Referring now to the drawings, and more particularly to FIGS. 1 through 7, where similar reference characters denote corresponding features consistently throughout the figures, there are shown embodiments herein. The production of high-quality graphene and the manufacture of semiconductor devices, integrated circuits (IC) devices, microelectromechanical systems (MEMS), nanoelectromechanical systems (NEMS), flat panel displays, optoelectronics devices, data storage devices, magneto electronic devices, magneto optic devices, packaged devices, solar devices, and the like entails the integration and sequencing of many unit processing steps. For example, epitaxial graphene typically includes a series of processing steps such as cleaning, surface preparation, deposition, and other related unit processing steps. The precise sequencing and integration of the unit processing steps enable the formation of high-quality graphene (e.g., uniform layers of epitaxial growth on a substrate, uniform graphene monolayer) meeting desired performance specifications such as uniformity. Other methods of increasing productivity and decreasing manufacturing costs include the use of batch reactors whereby multiple monolithic substrates can be processed in parallel. In these processing steps, a monolithic substrate or batch of monolithic substrates are processed uniformly; i.e., in the same fashion with the same resulting physical, chemical, electrical, and the like properties across a given monolithic substrate.

The embodiments herein support and enable efficient combinatorial processing. For example, in an embodiment described below, combinatorial processing provides rapid evaluation of graphene production operations and graphene properties. Some exemplary graphene production operations include operations for adding (e.g., depositions) layers, defining features, preparing layers (e.g., cleans), doping, etc. In such an embodiment, the systems supporting the combinatorial processing are flexible to accommodate the demands for running the different processes either in parallel, serial, or some combination of the two.

As used herein, combinatorial processing may include any processing (e.g., graphene production) that varies the processing conditions in two or more regions of a substrate. A substrate may be, for example, a production substrate (e.g., a substrate having a thin catalyst layer of nickel or a thin copper film, which, according to one embodiment, can be approximately between 200 and 700 nanometers thick), or a characterization substrate (e.g., glass, quartz, or any other transparent substrate). A region of a substrate may be any portion of the substrate that is somehow defined, for example by dividing the substrate into regions having predetermined dimensions or by using physical barriers, such as air curtains, over the substrate. The region may or may not be isolated from other regions. For example, a substrate may be divided into two or more regions, each of which may or may not include graphene sheets transferred thereto.

As described in the examples above, combinatorial processing, when applied to graphene production operations, enables multiple experiments to be performed on a single substrate. Embodiments herein, however, are not limited merely to graphene production. Equipment for performing the combinatorial processing and characterization of the combinatorial test substrates (e.g., production substrates, characterization substrates, etc.) must support the efficiency offered through the combinatorial processing operations.

For example, the process of forming test substrates to combinatorially test materials, processes, and devices is described herein. Combinatorial processing enables multiple experiments to be performed on a single substrate and the rapid evaluation of graphene production operations and materials. The test substrates are designed to run the different combinatorial processes either in parallel, serial, or some combination of the two. These methodologies all incorporate the formation of site-isolated regions using a combinatorial processing tool and the use of these site-isolated regions to form the test area. Therefore, multiple regions/test areas may be rapidly formed on a single substrate for use in combinatorial methodologies. Any of the individual processes of the methods described may be varied combinatorially to test varied process conditions or materials.

Use of combinatorial-based rapid device prototyping methods permits fabrication, comprehensive characterization, and analysis of hundreds of unique devices (e.g., graphene transistors, integrated circuits, etc.) and systems (e.g., MEMS, graphene bio-devices, ultra-capacitors, etc.) on a weekly basis to dramatically increase productivity and learning rates. For example, knowledge about alternative device structures, process integration schemes, and material compositions can be systematically explored at speeds that would otherwise be impossible using traditional methods and tools.

Figure 1:
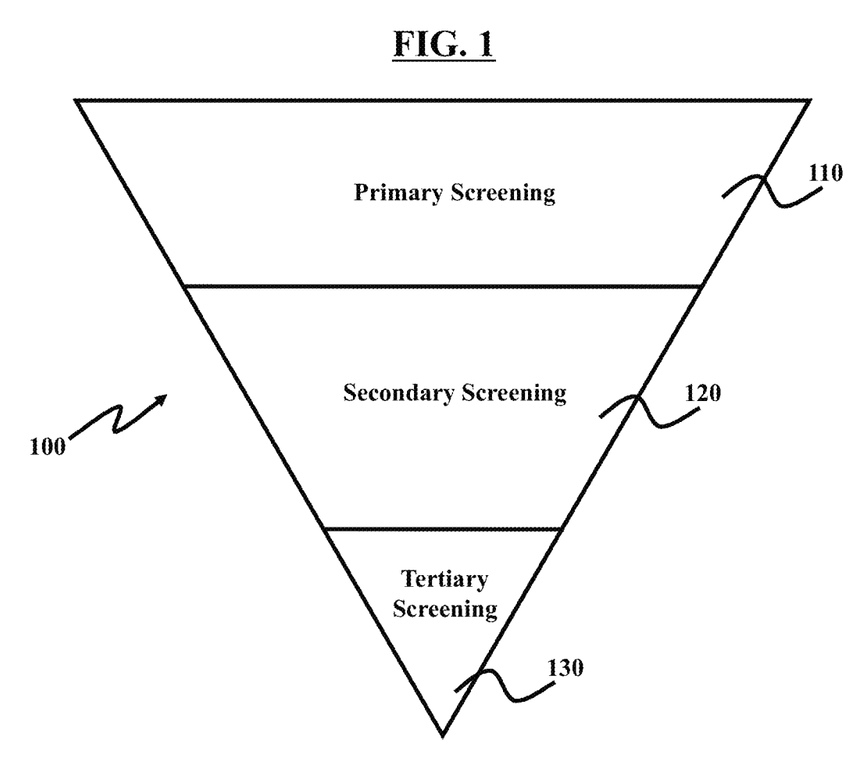
FIG. 1 illustrates a schematic diagram of a combinatorial screening process according to an embodiment herein.

As described above, during one embodiment of combinatorial processing, each wafer is subjected to many different process conditions. FIG. 1 illustrates an example of such a combinatorial screening process. As shown in FIG. 1, combinatorial screening process 100 includes primary screening process (110), secondary screening process (120), and tertiary screening process (130). In FIG. 1, for example, numerous material compositions (e.g., 18 spots or 46 spots on a single wafer, where each spot is a unique material composition or graphene material) are systematically explored on a single wafer during an initial primary screening process (110) at speeds that would otherwise be impossible using traditional methods and tools. In other words, in the embodiment shown in FIG. 1, the primary screening process (110) is an initial screening that processes many samples (e.g., using chemical vapor deposition (CVD) on a copper film) to rule out materials for further screening. Once the best materials, process conditions, or process integration are identified using initial combinatorial screening methods (e.g., during the primary screening process (110)), that material is then scaled up to characterize that material and/or conditions (e.g., graphene uniformity) during a secondary screening stage (e.g., the secondary screening process (120)). Furthermore, according to one embodiment herein, additional testing may take place during the tertiary screening process (130). During the tertiary screening process (130), for example, the materials and/or process conditions that were not filtered out during the primary screening process (110) and the secondary screening process (120) are scaled up to a device size. Furthermore, due to the speed of the characterization test (e.g., graphene uniformity, as described in further detail below) occurring in the secondary screening process (120), material and/or conditions that pass both the primary screening process (110) and the secondary screening process (120) can rapidly proceed to the tertiary screening process (130) if desired and applicable. Consequently, to test the uniformity of these material compositions, the embodiments herein utilize an improved measurement tool to enable the collection information more rapidly.

For example, as described in further detail below, the embodiments herein improve the combinatorial screening of graphene materials (e.g., chemical vapor deposition (CVD) on nickel or thin copper films) and the characterization those formulations. During an initial screening (e.g., primary screening process (110)), many samples (e.g., graphene materials) are tested by using thin copper (e.g., approximately between 200 and 700 nm) test wafers (e.g., as supplied by Advantiv Technologies, Inc. Fremont Calif., USA). This initial screening may have simple criteria (e.g., 5% improvement in sheet resistance) to allow a quick evaluation and thereby quickly rule out materials that will not undergo the second stage of testing (e.g., in the secondary screening process (120)). During the secondary screening process (120), a variety of more specific characterization methods may be performed on the graphene materials identified in the primary screening process (110) on fabricated patterned/metallized surfaces. Such characterization methods include parametric tests and reliability tests. Sample criteria to evaluate such graphene materials include, but are not limited to: uniform graphene layers, a <2 order leakage increase, a <10% resistance increase, a <10% capacitance increase. After performing such characterization methods on the graphene materials, those materials that pass certain criteria (e.g., the sample criteria discussed above) are then passed on to the tertiary screening process (130) that scales the graphene material to actual devices.

Contrary to conventional systems (e.g., traditional tests to characterize graphene uniformity), embodiments herein are quickly (e.g., within seconds) able to quantify the uniformity of a graphene sheet (e.g., determine the number of layers of graphene in the graphene sheet). For example, after combinatorial processing of material compositions on a single wafer, characterization embodiments described herein are a non-destructive means to quantitatively determine the uniformity of graphene (e.g., number of layers in a graphene sheet). Non-destructive testing allows for the testing of the same sample using multiple testing techniques. Such a technique is not possible in conventional processes given the testing parameters used in conventional solutions.

Figure 2A:
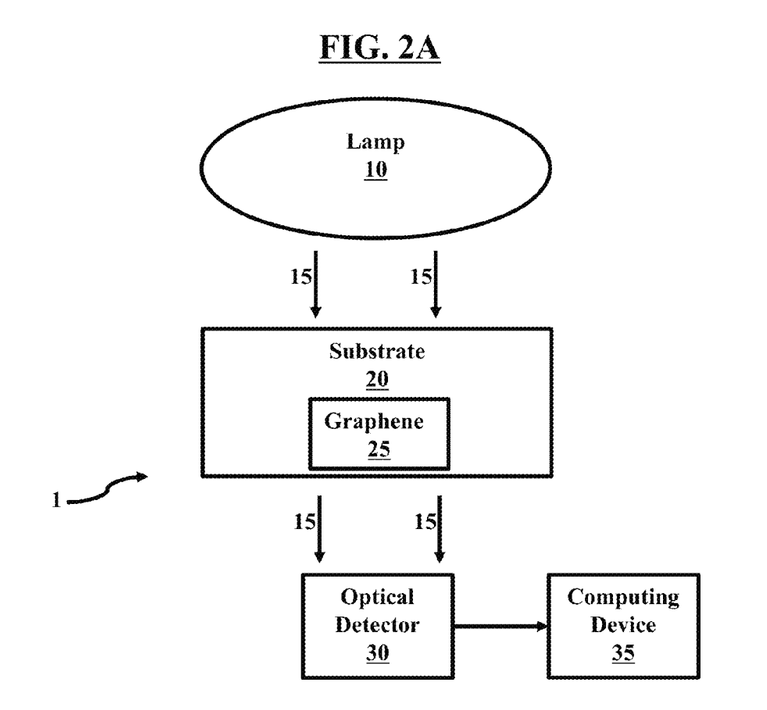
FIG. 2A illustrates a block diagram of a characterization apparatus according to an embodiment herein.

FIG. 2A, with reference to FIG. 1, illustrates a block diagram of a characterization apparatus according to an embodiment herein. According to the embodiment shown in FIG. 2A, characterization apparatus 1 includes a lamp 10 emitting light 15 through a substrate 20 that includes a graphene sheet 25. After passing through graphene sheet 25 on substrate 20, light 15 is detected by an optical detector 30 that is operatively coupled to a computing device 35. According to one embodiment herein, light 15 has a known wavelength in the visible spectrum (e.g., approximately 550 nm). Moreover, substrate 20 (e.g., quartz) is sufficiently transparent to allow predictable transmittance of light 15 therethrough and thereby not affect a transmittance calculation of graphene sheet 25 performed by computing device 35 (as described below). Optical detector 30 receives incoming light 15 and detects an amount of light received at a particular wavelength (e.g., 550 nm). As described in further detail below, computing device 35 calculates the opacity of graphene sheet 25 using the amount of incoming light 15 detected by optical detector 30 to quantify the thickness of graphene sheet 25 (e.g., determine the number of layers in graphene sheet 25). According to one embodiment herein, computing device 35 calculates the variance (e.g., statistical variance) in a number of layers, or thickness, across the graphene sheet (e.g., graphene sheet 25) to determine the uniformity of the graphene sheet (e.g., graphene sheet 25). The thickness of the graphene sheet can also be used to determine the properties of the graphene because the graphene properties are related to its thickness. Using these measurements it is possible to identify which processing methods can be used to produce uniformly deposited graphene having particular properties.

Figure 2B:
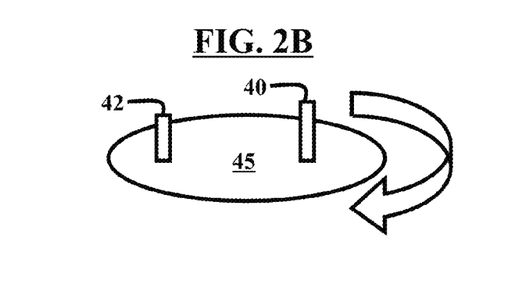
FIG. 2B illustrates a schematic diagram of a rotating platform according to an embodiment herein.

In addition, according to an embodiment shown in FIG. 2B, optical detector 30 and computing device 35 are logically combined into a transmittance detector 40 to calculate the transmittance of graphene sheet 25. FIG. 2B, with reference to FIGS. 1 and 2A, illustrates a schematic diagram of a rotation platform 45 according to an embodiment herein. As shown in FIG. 2B, rotation platform 45 includes transmittance detector 40 and another testing device 42 (e.g., a quantum efficiency detector). As a rotating platform, rotation platform 45 provides efficient use of testing equipment (e.g., characterization apparatus 1) by permitting performance of multiple tests on the same physical equipment. In the embodiment shown in FIG. 2B, rotation platform 45, when combined with transmittance detector 40 and testing device 42, provides spatial efficiency (e.g., the physical footprint of a single characterization apparatus vs. multiple characterization apparati) and throughput (e.g., promoting automation and temporal efficiency by avoiding complex movements (e.g., requiring human input) to perform multiple tests) through its configuration.

Figure 3A:
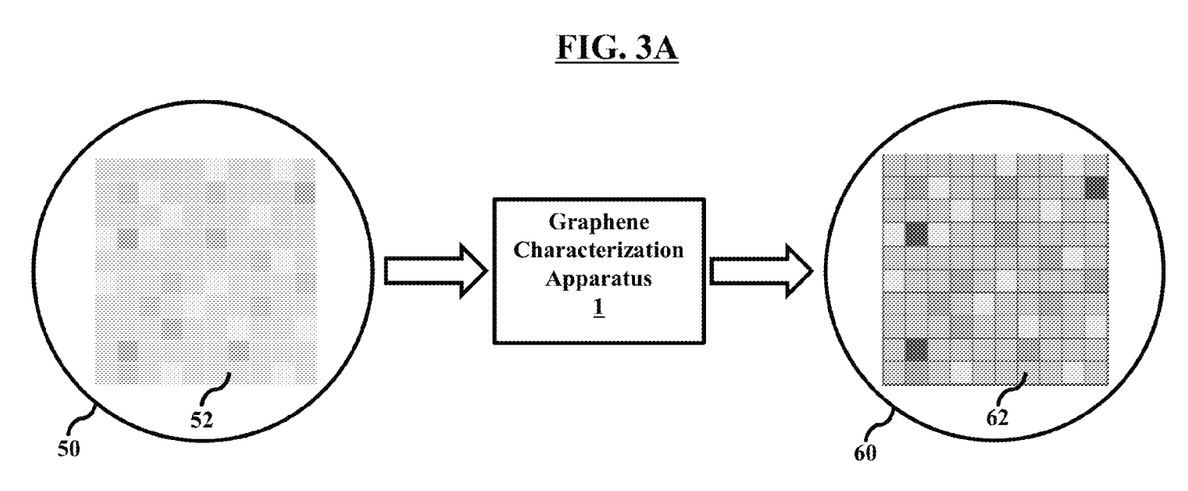
FIG. 3A illustrates a schematic diagram of a characterization apparatus according to an embodiment herein.
Figure 3B:
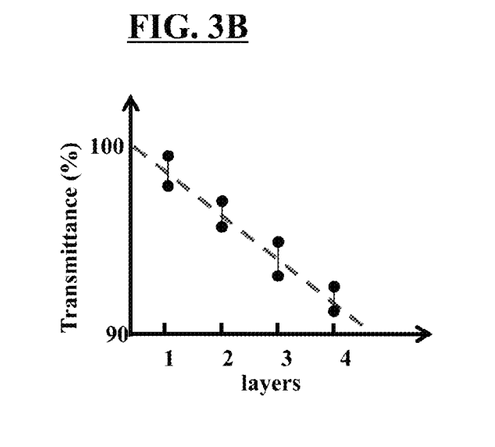
FIG. 3B illustrates a graphical representation of sample data produced according to an embodiment herein.

FIG. 3A, with reference to FIGS. 1 through 2B, illustrates a schematic diagram of a characterization test according to an embodiment herein. As shown in FIG. 3A, a wafer 50, with multiple graphene sheets 52 deposited thereon, is analyzed by graphene characterization apparatus 1. Based on the results obtained by graphene characterization apparatus 1, graphene characterization image 60 is produced. According to one embodiment herein, graphene characterization image 60 includes a graphene uniformity map 62 that describes graphene sheet 52. For example, in one embodiment graphene map 62 describes the transmittance of the individual graphene sheets (e.g., graphene sheet 25) on graphene sheet 52, number of layers in the individual graphene sheets (e.g., graphene sheet 25) on graphene sheet 52, or the graphene uniformity of graphene sheet 52. According to one embodiment herein, sample data from the calculations performed by graphene characterization apparatus 1 to determine the transmittance and number of layers in graphene sheet 52 are shown in FIG. 3B. As shown in FIG. 3B, as the number of layers in graphene sheet 52 increases, the transmittance decreases.

As described above, according to one embodiment herein, graphene sheet 52 includes multiple graphene sheets (e.g., an individual graphene sheet 25) are on a single substrate (e.g., wafer 50). In other words, the embodiments herein may vary the substrate (e.g., wafer 50), the materials, processes, and process sequences over the entire substrate. Thus, the testing finds optimums in regions of the substrate (e.g., wafer 50) without interference from process variation differences between processes that are meant to be the same. It should be appreciated that a region may be adjacent to another region in one embodiment or the regions may be isolated and, therefore, non-overlapping. When the regions are adjacent, there may be a slight overlap wherein the materials or precise process interactions are unknown, however, a portion of the regions, normally at least 60% or more of the area, is uniform and all testing occurs within that region. Further, the potential overlap is only allowed with materials of processes that will not adversely affect the result of the tests. Both types of regions are referred to herein as regions or discrete regions.

It should be appreciated that various other combinations of conventional and combinatorial processes can be included in the processing sequence with regard to FIG. 3A. That is, the combinatorial process sequence integration can be applied to any desired segments and/or portions of an overall process flow. Characterization, including uniformity, physical, chemical, acoustic, magnetic, electrical, optical, etc. testing, can be performed after each process operation, and/or series of process operations within the process flow as desired. The feedback provided by the testing is used to select certain materials, processes, process conditions, and process sequences and eliminates others. Furthermore, the above flows can be applied to entire monolithic substrates (e.g., substrate 20) or portions of monolithic substrates (e.g., wafer 50).

Figure 3C:
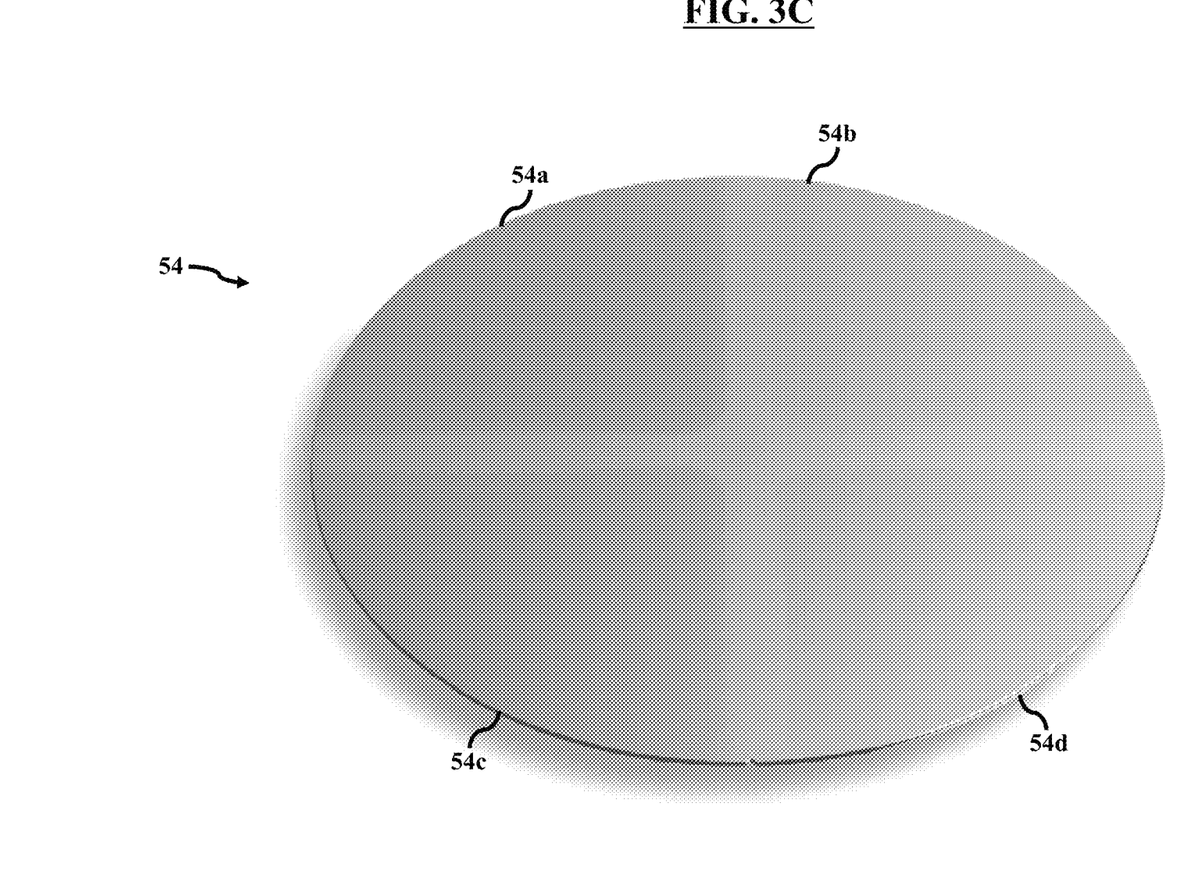
FIG. 3C illustrates a substrate with quadrant-based deposition according to an embodiment herein.

FIG. 3C, with reference to FIGS. 1 through 3B, illustrates a substrate 54 with quadrant-based deposition according to an embodiment herein. Substrate 54, shown in FIG. 3C, is an example of a monolithic substrate with portions thereof subjected to different process conditions. As shown in FIG. 3C, the four different process conditions are configured as four separate quadrants (e.g., quadrants 54a, 54b, 54c, and 54d) on substrate 54. The portions of substrate 54 subjected to different process conditions, however, are not limited to a quadrant configuration and other embodiments herein configure those portions of substrate 54 subjected to different process conditions differently (e.g., the regions may be shaped differently). While not shown in FIG. 3C, according to one embodiment herein, the deposition to different portions of substrate 54 (e.g., in quadrants 54a, 54b, 54c, and 54d) is performed using a high temperature combinatorial chemical vapor deposition (CVD) tool. Moreover, according to one embodiment, such a high temperature combinatorial CVD tool varies the material (e.g., graphene material) and process conditions (e.g., temperature) within different quadrants using a showerhead, for example, that creates the separate regions (e.g., quadrant 54a, 54b, 54c, and 54d).

Figure 4:
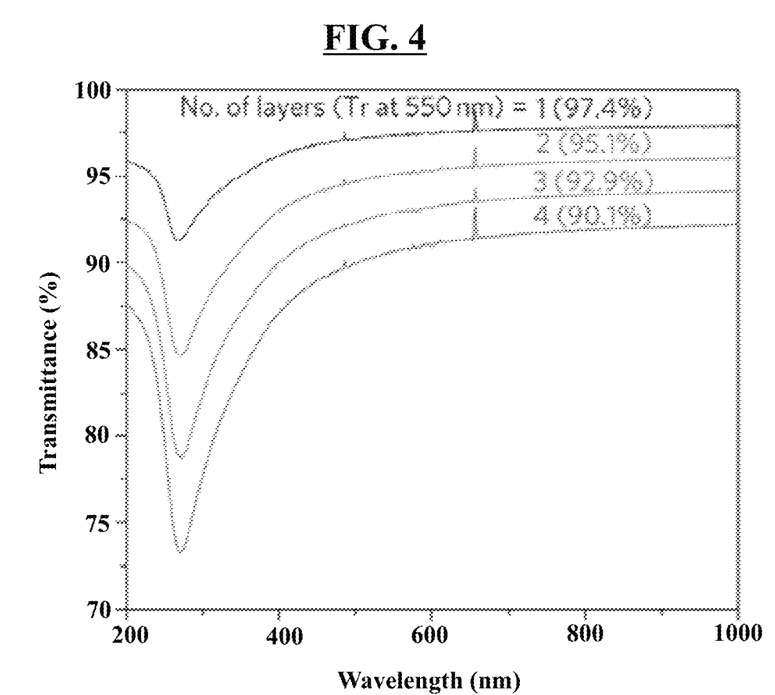
FIG. 4 illustrates another graphical representation of sample data produced according to an embodiment herein.

FIG. 4, with reference to FIGS. 1 through 3C, illustrates a graph of sample data produced according to an embodiment herein. In particular, FIG. 4 illustrates sample data received by a computing device (e.g., computing device 35) from an optical detector (e.g., optical detector 30) and in calculations performed by the computing device (e.g., computing device 35) to determine the number of layers in the tested graphene sheet (e.g., graphene sheet 25). As shown, four graphene sheets (e.g., graphene sheet 25) were tested, producing four data curves. According one embodiment herein, a predetermined graphene opacity value (e.g., approximately 2.3) at a predetermined wavelength (e.g., approximately 550 nm) of light (e.g., light 15) is used in computing device 35 to calculate a number of layers in a graphene sheet (e.g., graphene sheet 25). In other words, the embodiment shown in FIG. 4 determines that, for approximately every 2.3% reduction in transmittance at a specific wavelength (e.g., approximately 550 nm) from a baseline (e.g., the transmittance of light 15 through substrate 20 alone) there is an additional layer in the tested graphene sheet (e.g., graphene sheet 25). According to one embodiment herein, as shown in FIG. 3B, the calculation to determine the number of layers of a graphene sheet (e.g., graphene sheet 25) from the transmittance through the graphene sheet (e.g., graphene sheet) is a linear calculation. For example, according to one embodiment herein, a computing device (e.g., computing device 35) divides a transmittance loss (e.g., the difference between by the transmittance of light 15 through substrate 20 alone and the received transmittance of light 15 as it passed through substrate 20 and graphene sheet 25, as detected by optical detector 30) by a predetermined value (e.g., the opacity of graphene at a specific wavelength, such as approximately 2.3) and the number of layers in a graphene sheet (e.g., graphene sheet 25) includes the integer component of a remainder of this division. Thus, in the graph shown in FIG. 4, the tested graphene sheet (e.g., graphene sheet 25) varies from one to four layers.

Figure 5:
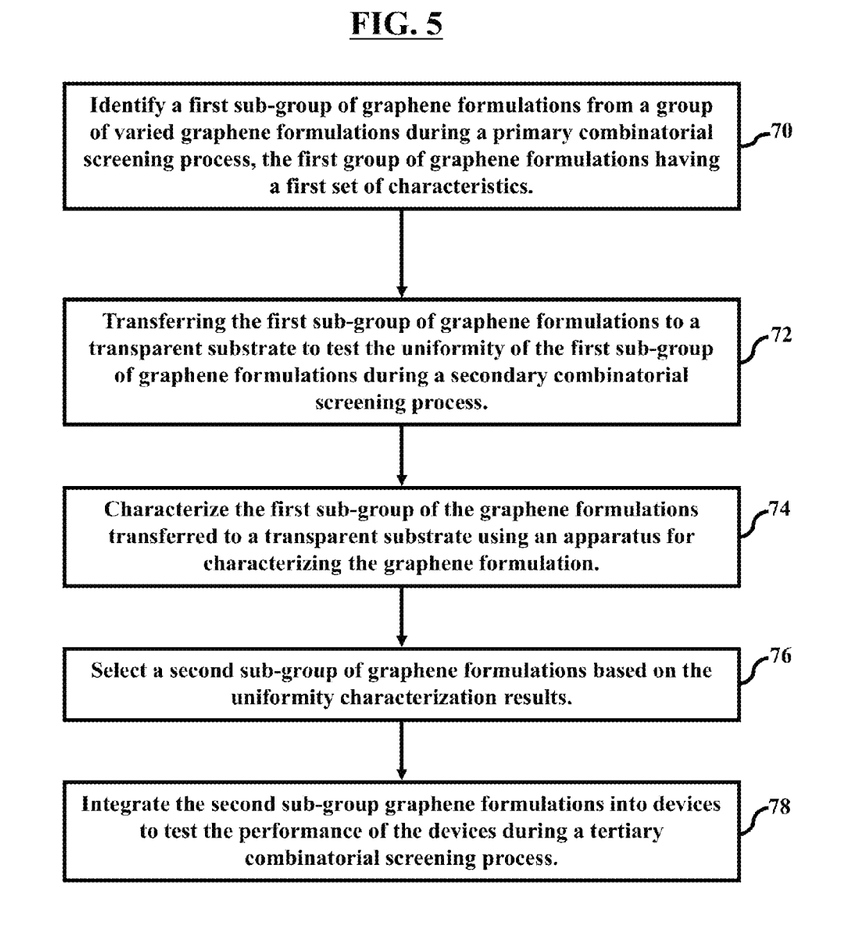
FIG. 5 illustrates a flowchart for a combinatorial testing method according to an embodiment herein.

FIG. 5, with reference to FIGS. 1 through 4, illustrates a flow diagram of a combinatorial testing method according to an embodiment herein. According to one embodiment herein, FIG. 5 illustrates a method of processing that includes a step (70) of identifying a first sub-group of graphene materials (e.g., graphene sheet 25) from a group of varied graphene materials (e.g., graphene sheet 25) during a primary combinatorial screening process (e.g., process (110)), the first group of graphene materials (e.g., graphene sheet 25) having a first set of characteristics. The next step (72) involves transferring the first sub-group of graphene materials to a transparent substrate (e.g., substrate 20) to test the uniformity of the first sub-group of graphene materials (e.g., graphene sheet 25) during a secondary combinatorial screening process (e.g., process (120)). Thereafter, step (74) includes characterizing the first sub-group of graphene materials (e.g., graphene sheet 25) transferred to the transparent substrate (e.g., substrate 20) using an apparatus 1 (e.g., shown in FIG. 2) for characterizing the graphene materials, where the apparatus 1 includes a lamp (e.g., lamp 10) emitting a light (e.g., light 15) of a known wavelength (e.g., approximately 550 nm), wherein the light (e.g., light 15) strikes and passes through (e.g., as shown in FIG. 2) the transparent substrate (e.g., substrate 20) and the graphene materials (e.g., graphene sheet 25), an optical detector (e.g., optical detector 30) detecting the light (e.g., light 15) from the lamp (e.g., lamp 10) after the light (e.g., light 15) passes through the transparent substrate (e.g., substrate 20) and the graphene materials (e.g., graphene sheet 25), and an computing device (e.g., computing device 35) calculating a characterization of the graphene materials (e.g., graphene sheet 25) from an amount of light (e.g., light 15) at the known wavelength (e.g., approximately 550 nm) that passed through the transparent substrate (e.g., substrate 20) and the graphene materials (e.g., graphene sheet 25) to produce uniformity characterization results (e.g., as shown in FIGS. 3B and 4). The next step (76) involves selecting a second sub-group of graphene materials (e.g., graphene sheet 25) based on the uniformity characterization results (e.g., as shown in FIG. 4). Finally, step (78) provides integrating the second sub-group of graphene materials (e.g., graphene sheet 25) into devices to test the performance of the devices during a tertiary combinatorial screening process (e.g., the tertiary screening process (130) of FIG. 1). In one embodiment, the graphene may be integrated into a logic device such as a transistor channel.

In FIG. 5, the graphene production may be performed by a high temperature chemical vapor deposition (CVD) (e.g. approximately between 700° C. to 1200° C.) and varying at least one of materials, process conditions, unit processes, and process sequences associated with the graphene production. The graphene material may be deposited on any substrate having a thin metal catalyst layer and capable of withstanding high temperatures (e.g. approximately 1000° C.) and rapid fluctuations in temperature. For example, the varied process conditions during CVD production of graphene (e.g., graphene sheet 25) may be varying the type or amount of precursor gas (e.g. the carbon containing gases or the hydrogen gas used to form graphene) and a carrier gas, varying the flow rates of the gases, varying the temperature at which the graphene is deposited, varying the pressure at which the graphene is deposited (e.g., approximately 40 mtorr to 1 atmosphere), varying the quench rate of the deposition by rapidly dropping the temperature (e.g., reducing the temperature by 10° C. per second), or varying the lower temperature at which the growth is quenched (e.g., approximately between 20° C. to 25° C.).

Also, the catalyst used for the growth of graphene on the substrate may be varied either in the type of metal (e.g. copper or nickel or an alloy) or the thickness of the metal layer on the substrate. After the deposition of the graphene on the substrate having a metal catalyst layer, the graphene sheet is transferred to a transparent substrate in order to perform the characterization. In addition, characterizing (74) the first sub-group of graphene materials (e.g., graphene sheet 25) transferred to the transparent substrate (e.g., substrate 20) may include graphene uniformity characterization. In addition, the first group (70) of graphene materials (e.g., graphene sheet 25) having a first set of characteristics include graphene materials that vary a gas and a carrier used during chemical vapor deposition (CVD) production of graphene (e.g., graphene sheet 25). Moreover, selecting (76) a second sub-group of graphene materials (e.g., graphene sheet 25) based on the uniformity characterization results may include selecting graphene materials from the first sub-group (70) with graphene uniformity values exceeding a predetermined threshold from the uniformity characterization results.

In FIG. 5, calculating (72) a characterization of the graphene material may include providing a substrate baseline transmittance comprising a baseline transmittance of the transparent substrate (e.g., substrate 20), providing a graphene transmittance, wherein the graphene transmittance includes a transmittance of the graphene sheet (e.g., graphene sheet 25) and transparent substrate (e.g., substrate 20), and calculating a number of layers from the graphene transmittance. Moreover, the calculating the number of layers from the graphene transmittance may include determining a transmittance loss by subtracting the graphene transmittance from the substrate baseline transmittance, and dividing the transmittance loss by a predetermined value, wherein the number of layers in a graphene sheet (e.g., graphene sheet 25) includes an integer component of a remainder of the division. Furthermore, the predetermined value may be 2.3. Additionally, the transparent substrate (e.g., substrate 20) may include quartz. In addition, as an example of the known wavelength of the light used for the measurements described above, the known wavelength may include a range of wavelengths (e.g., the range of visible light) or may approximately be equal to 550 nanometers.

Figure 6:
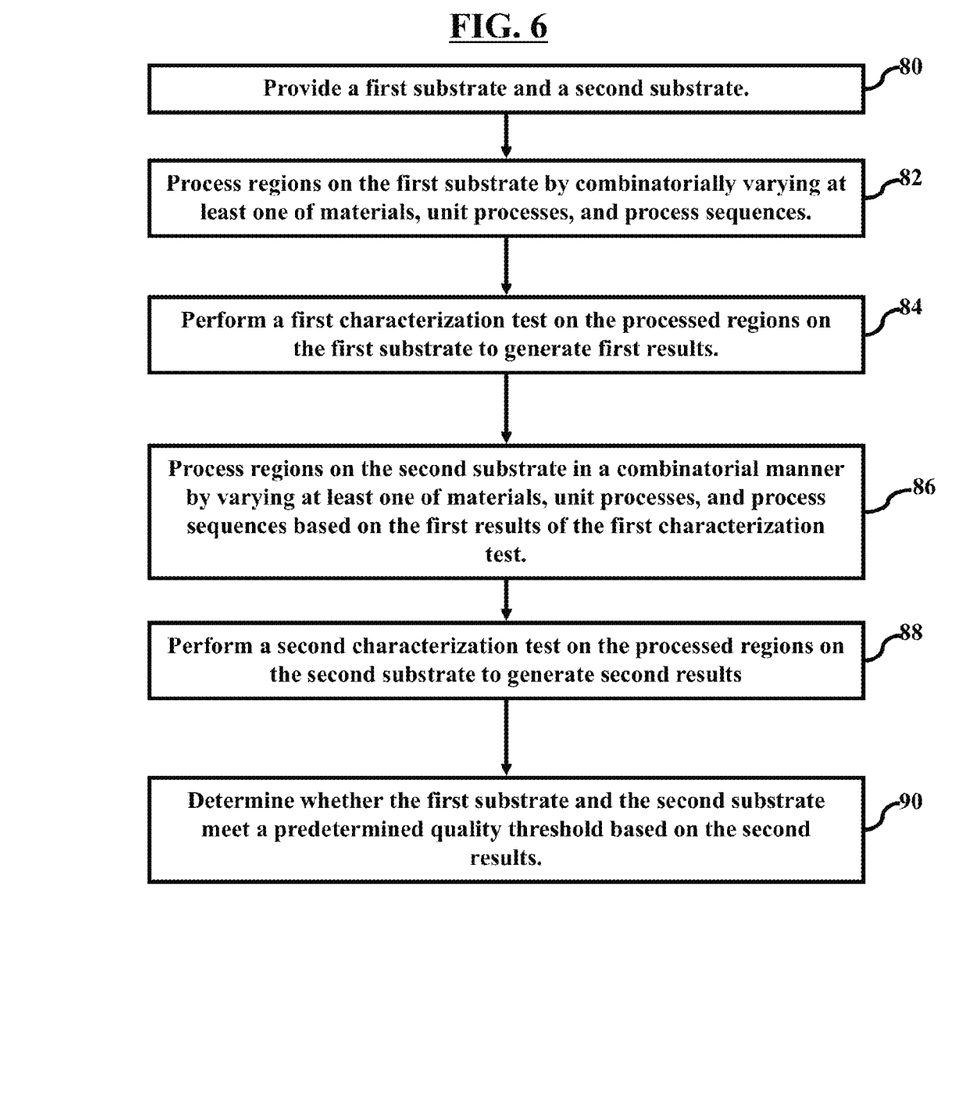
FIG. 6 illustrates a flowchart of a test method according to an embodiment herein.

FIG. 6, with reference to FIGS. 1 through 5, illustrates a flowchart of a testing method according to the embodiments herein. According to one embodiment herein, the method shown in FIG. 6 is for evaluating materials, process conditions, unit processes, and process sequences graphene production and includes providing (80) a first substrate (e.g., substrate 20) and a second substrate (e.g., wafer 50), each substrate 20, 50 includes a predetermined baseline transmittance value at a predetermine wavelength of light (e.g., light 15); processing (82) regions on the first substrate (e.g., substrate 20) by combinatorially varying at least one of materials, process conditions, unit processes, and process sequences associated with graphene production; performing (84) a first characterization test on the processed regions on the first substrate (e.g., substrate 20) to generate first results; processing (86) regions on a second substrate (e.g., silicon wafer 50) in a combinatorial manner by varying at least one of materials, process conditions, unit processes, and process sequences associated with the graphene production based on the first results of the first characterization test; performing (88) a second characterization test on the processed regions on the second substrate (e.g., wafer 50) to generate second results; and determining (90) whether the first substrate (e.g., substrate 20) and the second substrate (e.g., wafer 50) meet a predetermined quality threshold based on the second results.

In FIG. 6, the first characterization test (84) and the second characterization test (88) includes determining a number of layers in a graphene sheet (e.g., graphene sheet 25) on at least one of the first substrate (e.g., substrate 20) and the second substrate (e.g., wafer 50). In addition, the determining a number of layers in a graphene sheet (e.g., graphene sheet 25) may include providing a substrate baseline transmittance comprising a baseline transmittance of at least one of the first substrate (e.g., substrate 20) and the second substrate (e.g., wafer 50); providing a graphene transmittance, wherein the graphene transmittance includes a transmittance of the graphene sheet (e.g., graphene sheet 25) and at least one of the first substrate (e.g., substrate 20) and the second substrate (e.g., wafer 50), and calculating the number of layers from the graphene transmittance. Furthermore, the calculating the number of layers from the graphene transmittance may include determining a transmittance loss by subtracting the graphene transmittance from the substrate baseline transmittance, and dividing the transmittance loss by a predetermined value, wherein the number of layers in a graphene sheet (e.g., graphene sheet 25) includes an integer component of a remainder of the division. Moreover, the predetermined value may be 2.3. Additionally, at least one of the first substrate (e.g., substrate 20) and the second substrate (e.g., wafer 50) may include quartz.

In addition, in the method shown in FIG. 6, determining (90) whether at least one of the first substrate (e.g., substrate 20) and the second substrate (e.g., wafer 50) meet a predetermined quality threshold based on the second results may include determining the uniformity of a graphene sheet (e.g., graphene sheet 25) on at least one of the first substrate and the second substrate. Furthermore, the determining the uniformity of a graphene sheet (e.g., graphene sheet 25) on at least one of the first substrate (substrate 20) and the second substrate (e.g., wafer 50) includes determining a variance in a number of layers across the graphene sheet (e.g., graphene sheet 25). Moreover, varying at least one of materials, process conditions, unit processes, and process sequences associated with the graphene production includes varying a temperature during the graphene production and the varying a temperature during the graphene production includes varying the temperature approximately between 700° C. and 1200° C. Additionally, the graphene production may include chemical vapor deposition (CVD) and varying at least one of materials, process conditions, unit processes, and process sequences associated with the graphene production includes varying a gas and a carrier (not shown) used during CVD production of graphene (e.g., graphene sheet 25).

Figure 7:
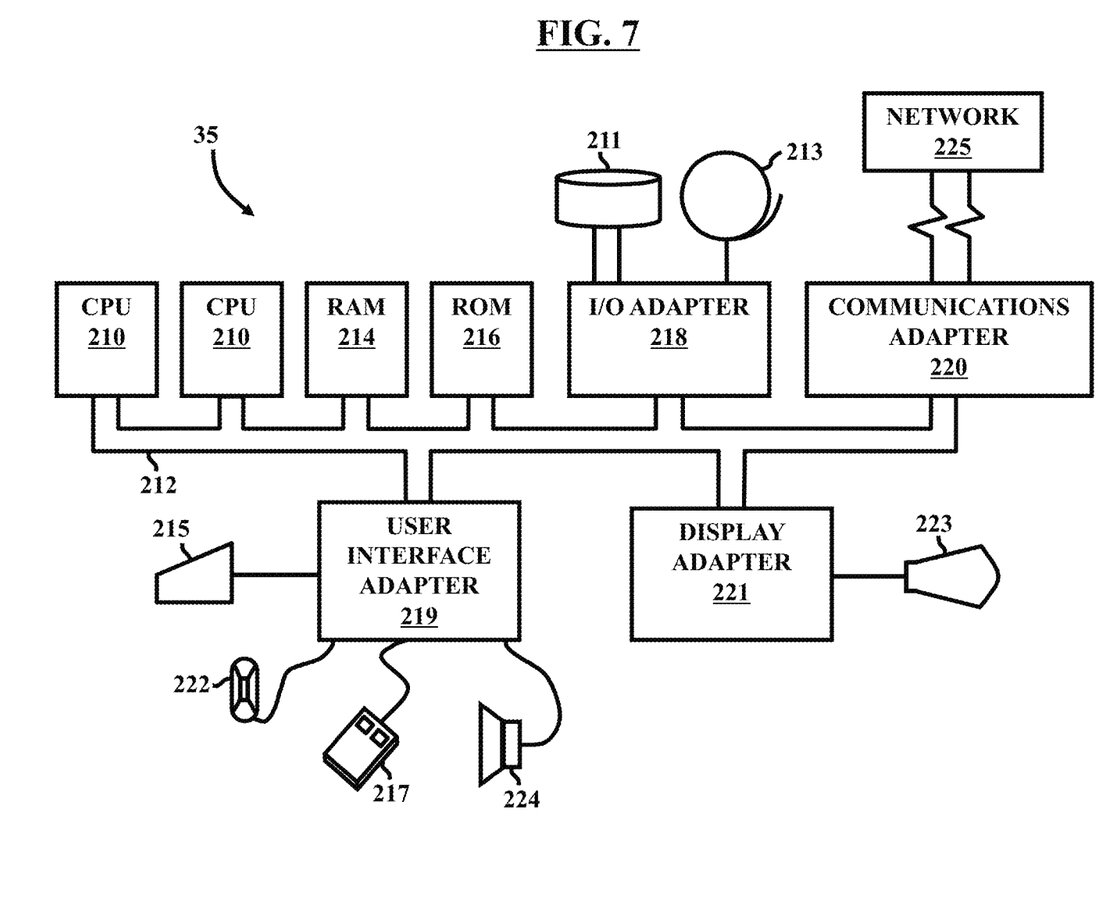
FIG. 7 illustrates a computing system according to an embodiment herein.

A representative hardware environment for practicing the embodiments herein is depicted in FIG. 7, with reference to FIGS. 1 through 6. This schematic drawing illustrates a hardware configuration of an information handling/computer system 35 in accordance with one embodiment herein. The system 35 includes at least one processor or central processing unit (CPU) 210. The CPUs 210 are interconnected via system bus 212 to various devices such as a random access memory (RAM) 214, read-only memory (ROM) 216, and an input/output (I/O) adapter 218. The I/O adapter 218 can connect to peripheral devices, such as disk units 211 and tape drives 213, or other program storage devices that are readable by the system 35. The system 35 can read the inventive instructions on the program storage devices and follow these instructions to execute the methodology of the embodiments herein. The system 35 further includes a user interface adapter 219 that connects a keyboard 215, mouse 217, speaker 224, microphone 222, and/or other user interface devices such as a touch screen device (not shown) to the bus 212 to gather user input. Additionally, a communication adapter 220 connects the bus 212 to a data processing network 225, and a display adapter 221 connects the bus 212 to a display device 223 which may be embodied as an output device such as a monitor, printer, or transmitter, for example.

One embodiment of the combinatorial screening process described above (e.g., FIGS. 1 and 5) enables multiple experiments to be performed on a single substrate 20 and the rapid evaluation of graphene production operations and semiconductor materials. The graphene test substrates 20 are designed to run the different combinatorial processes either in parallel, serial, or some combination of the two. For example, the embodiments herein allow simultaneous testing of different types of graphene materials that can be combinatorially varied and evaluated. These methodologies all incorporate the formation of site-isolated regions using a combinatorial processing tool and the use of these site-isolated regions to form the graphene sheet 25. Therefore, multiple graphene materials may be rapidly formed on a single substrate 20 for use in combinatorial methodologies. Any of the individual processes of the methods described may be varied combinatorially to test varied process conditions or materials.

The use of combinatorial-based rapid device prototyping methods (e.g., as shown in FIGS. 1 and 5) permits fabrication, comprehensive characterization, and analysis of hundreds of unique graphene production operations and devices on a weekly basis to dramatically increase learning rates. Alternative device structures, process integration schemes, and materials compositions are systematically explored at speeds that would otherwise be impossible using traditional methods and tools.

Generally, the embodiments herein provide the ability to more efficiently screen and analyze an array of materials, processes, and process sequence integration schemes across a substrate 20 in order to more efficiently evaluate alternative materials, processes, and process sequence integration schemes for semiconductor manufacturing processes. Moreover, the embodiments herein provide high performance combinatorial characterization tools that quickly process and characterize combinatorial test substrates 20.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of several embodiments, those skilled in the art will recognize that the embodiments herein can be practiced with modification within the spirit and scope of the appended claims.

What is claimed is:

1. A method comprising:
   providing a substrate comprising multiple site-isolated regions on a non-transparent substrate,
      wherein each of the multiple site-isolated regions comprises a graphene material combinatorially varied from any other graphene material in a different one of the multiple site-isolated regions using at least one of varying materials, varying process conditions, varying unit processes, or varying process sequences associated with graphene production;
   testing the graphene material in each of the multiple site-isolated regions for a sheet resistance;
   identifying a first sub-group of the multiple site-isolated regions comprising the graphene materials based on meeting a sheet resistance criterion,
      wherein the first sub-group is identified from a group of the multiple site-isolated regions during a primary combinatorial screening process,
      wherein the first sub-group comprises graphene materials having a first set of characteristics;
   transferring said first sub-group of the graphene materials to a transparent substrate;
   testing the said first sub-group of the graphene materials for transmittance uniformity during a secondary combinatorial screening process,
      wherein testing the graphene material for transmittance uniformity is performed using an apparatus for characterizing the graphene materials,
      said apparatus comprising:
         a lamp emitting a light of a known wavelength,
            wherein said light strikes and passes through said transparent substrate and said graphene materials;
         an optical detector detecting said light from said lamp after said light passes through said transparent substrate and said graphene materials; and
         a computing device calculating transmittance uniformity of the graphene materials in each of the multiple site-isolated regions of the first sub-group based on an amount of light at said known wavelength that passed through said transparent substrate;
   identifying a second sub-group of graphene materials of the multiple site-isolated regions of the first sub-group based on meeting a transmittance uniformity criterion; and
   integrating said second sub-group of graphene materials into devices and testing said devices for device performance during a tertiary combinatorial screening process.

2. The method of claim 1, further comprising forming the graphene material in each of the multiple site-isolated regions while varying type and/or amount of a precursor gas and a carrier gas used during chemical vapor deposition (CVD) among the multiple site-isolated regions.

3. The method of claim 1, wherein identifying the second sub-group of graphene materials comprises:
   providing a substrate baseline transmittance comprising a baseline transmittance of said transparent substrate;
   providing a graphene transmittance for each of the graphene materials in the first sub-group,
      wherein said graphene transmittance comprises a transmittance of each of the graphene materials in the first sub-group and the transparent substrate; and
   calculating a number of layers from said graphene transmittance.

4. The method of claim 1, wherein said transparent substrate comprises quartz.

5. The method of claim 1, wherein said known wavelength equals 550 nanometers.

6. The method of claim 1, wherein the non-transparent substrate comprises one of nickel or copper.

7. The method of claim 1, wherein testing the said first sub-group of the graphene materials for transmittance uniformity during the secondary combinatorial screening process comprises rotating the substrate relative to the optical detector to align each of the multiple site-isolated regions with respect to the optical detector.

8. The method of claim 1, wherein identifying the second sub-group of graphene materials comprises producing a graphene map including one or more of:
   transmittance of each of the graphene materials in the first sub-group,
   a number of layers in each of the graphene materials in the first sub-group, or
   graphene uniformity of each of the graphene materials in the first sub-group.

9. The method of claim 1, wherein the multiple site-isolated regions do not overlap.

10. The method of claim 1, further comprising forming the graphene material in each of the multiple site-isolated regions while varying a deposition pressure while depositing in different ones of the multiple site-isolated regions.

11. The method of claim 1, further comprising forming the graphene material in each of the multiple site-isolated regions while varying a quench rate in different ones of the multiple site-isolated regions.

12. The method of claim 1, further comprising forming the graphene material in each of the multiple site-isolated regions using different catalysts in the multiple site-isolated regions.

13. The method of claim 2, wherein the multiple site-isolated regions are isolated from each other using air curtains during chemical vapor deposition (CVD).

14. The method of claim 2, wherein forming the graphene materials in each of the multiple site-isolated regions is performed using different temperatures in each of the multiple site-isolated regions.

15. The method of claim 2, wherein forming the graphene materials in each of the multiple site-isolated regions is performed using 700° C. to 1200° C.

16. The method of claim 3, wherein said calculating a number of layers from said graphene transmittance comprises:
    determining a transmittance loss by subtracting said graphene transmittance from said substrate baseline transmittance; and
    dividing said transmittance loss by a predetermined value, wherein said number of layers in said graphene sheet comprises an integer component of a remainder of said division.

17. The method of claim 12, wherein the different catalysts in the multiple site-isolated regions have different catalyst compositions.

18. The method of claim 12, wherein the different catalysts in the multiple site-isolated regions have different catalyst amounts.

19. The method of claim 16, wherein said predetermined value is 2.3.

\* \* \* \* \*